United States Patent
Hipskind et al.

(10) Patent No.: US 6,175,013 B1
(45) Date of Patent: *Jan. 16, 2001

(54) IMIDAZOLINYL TACHYKININ RECEPTOR ANTAGONISTS

(75) Inventors: Philip A. Hipskind, New Palestine, IN (US); J. Jeffry Howbert, Bellevue, WA (US); Brian S. Muehl, Indianapolis, IN (US)

(73) Assignee: Eli Lilly and Company, Indianapolis, IN (US)

( * ) Notice: Under 35 U.S.C. 154(b), the term of this patent shall be extended for 0 days.

This patent is subject to a terminal disclaimer.

(21) Appl. No.: 08/257,966

(22) Filed: Jun. 10, 1994

(51) Int. Cl.[7] .................. A61K 31/497; A61K 31/4178; C07D 403/02; C07D 233/04
(52) U.S. Cl. .................. 544/370; 514/254.05; 514/393; 514/399; 514/400; 514/402; 548/312.1; 548/350.1; 548/354.1; 548/355.1
(58) Field of Search .............................. 548/312.1, 354.1, 548/355.1, 350.1; 514/401, 399, 400, 393, 254.05; 544/370

(56) References Cited

U.S. PATENT DOCUMENTS 2,505,247   4/1950   Isler .............................. 548/354.1 X

FOREIGN PATENT DOCUMENTS

| 830 954 | 1/1952 | (DE) . |
| 0 545 478 | 6/1993 | (EP) . |
| 466 231 | 11/1975 | (SU) . |
| WO 94/10168 | 5/1994 | (WO) . |
| WO 95/14017 | 5/1995 | (WO) . |

OTHER PUBLICATIONS

Berger, J., "Dreikomponentenreaktionen. III. Nucleophile Substitutionen an Thiokohlensaure–S–ester–N–(.beta.–chloralkyl)–imidchloriden und C–chlor–N–(.beta.–chloralkyl)–N',N'–dialkylformamidiniumchloriden. Die Darstellung von 2–Alkylthio– and 2–Dialkylamino–.delta.2–azolinen," *Journal Fur Praktische Chemie*, vol. 311, No. 4 (1969); pp. 549–562.

Alegre, et al., "Aportaciones al estudio de algunos vasoconstrictores por pletismografia," *Circular Farmaceutica*, vol. 28, No. 229 (1970), pp. 261–272.

Matier, et al., "Antihypertensive agents. Synthesis and biological properties of 2–amino–4–aryl–2–imidazolines," *Journal of Medicinal Chemistry*, vol. 16, No. 8 (1973), pp. 901–908.

Hsu, et al., "Optically active derivatives of imidazolines, .alpha.–adrenergic blocking properties," *Journal of Medicinal Chemistry*, vol. 23, No. 11 (1980), pp. 1232–1235.

Weinhardt, et al., Synthesis and central nervous system properties of 2–[(alkoxycarbonyl)amino]–4(5)–phenyl–2–imidazolines, *Journal of Medicinal Chemistry*, vol. 27, No. 5 (1984), pp. 616–627.

Amemiya, et al., "Dehydrogenation of imidazolines to imidazoles with Pd–carbon," *Synthetic Communications*, vol. 20, No. 16 (1990), pp. 2483–2489.

Sun, et al., "A brominated (aminoimidazolinyl)indole from the sponge *discodermia polydiscus*," *Journal of Organic Chemistry*, vol. 56, No. 13 (1991), pp. 4307–4308.

Jones, et al., "1,3–Dipolar cycloadditions of 4,5–dihydroimidazoliumylides: new protocols for the synthesis of pyrrolidines and pyrrolo[1,2–a]pyrazines," *Journal of the Chemical Society*, Perkin Transactions 1, No. 20 (1993), pp. 2391–2393.

Jones, et al., "A new route to homochiral piperidines," *Tetrahedron Letters*, vol. 34, No. 39 (1993), pp. 6329–6332.

*Primary Examiner*—Floyd D. Higel
(74) *Attorney, Agent, or Firm*—Manisha A. Desai; Paul J. Gaylo

(57) ABSTRACT

This invention provides a series of substituted 2-imidazolines which are useful in the treatment or prevention of a physiological disorder associated with an excess of tachykinins. This invention also provides methods for the treatment of such physiological disorders as well as pharmaceutical formulations which employ these compounds.

16 Claims, No Drawings

IMIDAZOLINYL TACHYKININ RECEPTOR ANTAGONISTS

BACKGROUND OF THE INVENTION

Tachykinins are a family of peptides which share the common amidated carboxy terminal sequence, Phe-Xaa-Gly-Leu-Met-NH$_2$ hereinafter referred to as SEQ ID NO:1. Substance P was the first peptide of this family to be isolated, although its purification and the determination of its primary sequence did not occur until the early 1970's. Substance P has the following amino acid sequence, Arg-Pro-Lys-Pro-Gln-Gln-Phe-Phe-Gly-Leu-Met-NH$_2$ hereinafter referred to as SEQ ID NO:2.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Pentides*, 6 (Supplement 3):237–243 (1985) for a review of these discoveries. Neurokinin A has the following amino acid sequence, His-Lys-Thr-Asp-Ser-Phe-Val-Gly-Leu-Met-NH$_2$ hereinafter referred to as SEQ ID NO:3. The structure of neurokinin B is the amino acid sequence, Asp-Met-His-Asp-Phe-Phe-Val-Gly-Leu-Met-NH$_2$ hereinafter referred to as SEQ ID NO:4.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

In essence, this invention provides a class of potent non-peptide tachykinin receptor antagonists. By virtue of their non-peptide nature, the compounds of the present invention do not suffer from the shortcomings, in terms of metabolic instability, of known peptide-based tachykinin receptor antagonists.

SUMMARY OF THE INVENTION

This invention encompasses methods for the treatment or prevention of a physiological disorder associated with an excess of tachykinins, which method comprises administering to a mammal in need of said treatment an effective amount of a compound of Formula I

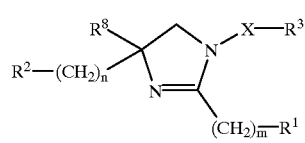

wherein:
  m is 0 or 1;
  n is 0 or 1;
  x is —(CHR$^4$)$_p$—(CHR$^6$)$_q$—, where,
  p is 0 or 1;
  q is 0 or 1; and
  R$^4$ and R$^6$ are independently selected from the group consisting of hydrogen and C$_1$–C$_3$ alkyl;
  R$^2$ is phenyl, 2- or 3-indolyl, 2- or 3-indolinyl, benzothienyl, benzofuranyl, or naphthyl;
    any one of which groups may be substituted with one or two moieties independently selected from the group consisting of halo, C$_1$–C$_3$ alkoxy, trifluoromethyl, C$_1$–C$_4$ alkyl, phenyl-C$_1$–C$_3$ alkoxy, and C$_1$–C$_4$ alkanoyl groups;
  R$^1$ is hydrogen, trityl, phenyl, diphenylmethyl, phenoxy, phenylthio, hexamethyleneiminyl, piperazinyl, piperidinyl, pyrrolidinyl, morpholinyl, indolinyl, indolyl, benzothienyl, benzofuranyl, quinolinyl, isoquinolinyl, tetrahydropyridinyl, reduced quinolinyl, reduced isoquinolinyl, phenyl-(C$_1$–C$_6$ alkylidenyl)-, phenyl-(C$_1$–C$_4$ alkoxy)-, quinolinyl-(C$_1$–C$_6$ alkylidenyl)-, isoquinolinyl-(C$_1$–C$_6$ alkylidenyl)-, reduced quinolinyl-(C$_1$–C$_6$ alkylidenyl)-, reduced isoquinolinyl-(C$_1$–C$_6$ alkylidenyl)-, benzoyl-(C$_1$–C$_6$ alkylidenyl)-, C$_1$–C$_4$ alkyl, or —NH—CH$_2$—R$^5$;
    any one of which R$^1$ groups may be substituted with halo, C$_1$–C$_4$ alkyl, C$_1$–C$_4$ alkoxy, trifluoromethyl, amino, C$_1$–C$_4$ alkylamino, or di(C$_1$–C$_4$ alkyl)amino;
    or any one of which R$^1$ groups may be substituted with phenyl, piperazinyl, C$_3$–C$_8$ cycloalkyl, benzyl, C$_1$–C$_4$ alkyl, piperidinyl, pyridinyl, pyrimidinyl, C$_2$–C$_6$ alkanoylamino, pyrrolidinyl, C$_2$–C$_6$ alkanoyl, or C$_1$–C$_4$ alkoxycarbonyl;
    any one of which groups may be substituted with halo, C$_1$–C$_4$ alkyl, C$_1$–C$_4$ alkoxy, trifluoromethyl, amino, C$_1$–C$_4$ alkylamino, di(C$_1$–C$_4$ alkyl)amino, or C$_2$–C$_4$ alkanoylamino;
  or R$^1$ is amino, a leaving group, hydrogen, C$_1$–C$_4$ alkylamino, or di(C$_1$–C$_4$ alkyl)amino;
  R$^5$ is pyridyl, anilino-(C$_1$–C$_6$ alkylidenyl)-, or anilinocarbonyl;
  R$^8$ is hydrogen or C$_1$–C$_6$ alkyl; and
  R$^3$ is phenyl, phenyl-(C$_1$–C$_6$ alkylidenyl)-, C$_3$–C$_8$ cycloalkyl, C$_5$–C$_8$ cycloalkenyl, C$_1$–C$_8$ alkyl, naphthyl, C$_2$–C$_8$ alkenyl, or hydrogen;
    any one of which groups except hydrogen may be substituted with one or two halo, C$_1$–C$_3$ alkoxy, C$_1$–C$_3$ alkylthio, nitro, trifluoromethyl, or C$_1$–C$_3$ alkyl groups;
or a pharmaceutically acceptable salt or solvate thereof.

In other embodiments this invention encompasses the novel compounds of Formula I and the salts and solvates of those compounds, as well as pharmaceutical formulations comprising at least one compound of Formula I, or a pharmaceutically acceptable salt or solvent of said compound, in combination with one or more pharmaceutically acceptable carrier, diluents, or excipients.

DETAILED DESCRIPTION AND PREFERRED EMBODIMENTS

The terms and abbreviations used in the instant examples have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "IR" refers to infrared spectroscopy; and "NMR" refers to nuclear magnetic resonance spectroscopy.

As used herein, the term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$–$C_6$ alkyl" includes within its definition the term "$C_1$–$C_3$ alkyl".

"$C_1$–$C_6$ alkylidenyl" refers to a straight or branched, divalent, saturated aliphatic chain of 1 to 6 carbon atoms and includes, but is not limited to, methylenyl, ethylenyl, propylenyl, isopropylenyl, butylenyl, isobutylenyl, t-butylenyl, pentylenyl, isopentylenyl, and hexylenyl.

"Halo" represents chloro, fluoro, bromo or iodo.

"$C_1$–$C_6$ alkylthio" represents a straight or branched alkyl chain having from one to six carbon atoms attached to a sulfur atom. Typical $C_1$–$C_6$ alkylthio groups include methylthio, ethylthio, propylthio, isopropylthio, butylthio and the like. The term "$C_1$–$C_6$ alkylthio" includes within its definition the term "$C_1$–$C_3$ alkylthio".

The term "$C_2$–$C_8$ alkenyl" as used herein represents a straight or branched, monovalent, unsaturated aliphatic chain having from two to eight carbon atoms. Typical $C_2$–$C_8$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

"$C_5$–$C_8$ cycloalkenyl" represents a hydrocarbon ring structure containing from five to eight carbon atoms and having at least one double bond within that ring, which is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$)alkylcarbamoyl, amino, $C_1$–$C_4$ alkylamino, di($C_1$–$C_4$)alkylamino or —(CH$_2$)$_a$—R$^c$ where a is 1, 2, 3 or 4 and R$^c$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

"$C_1$–$C_6$ alkylamino" represents a straight or branched alkylamino chain having from one to six carbon atoms attached to an amino group. Typical $C_1$–$C_6$ alkyl-amino groups include methylamino, ethylamino, propylamino, isopropylamino, butylamino, sec-butylamino and the like. "$C_1$–$C_6$ alkylamino" encompasses within this term "$C_1$–$C_4$ alkylamino".

"Di($C_1$–$C_4$ alkyl)amino" represents a straight or branched dialkylamino chain having two alkyl chains, each having independently from one to four carbon atoms attached to a common amino group. Typical di($C_1$–$C_4$)alkylamino groups include dimethylamino, ethylmethylamino, methylisopropylamino, t-butylisopropylamino, di-t-butylamino and the like.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_3$ alkoxy".

"$C_2$–$C_6$ alkanoyl" represents a straight or branched alkyl chain having from one to five carbon atoms attached to a carbonyl moiety. Typical $C_2$–$C_6$ alkanoyl groups include ethanoyl, propanoyl, isopropanoyl, butanoyl, t-butanoyl, pentanoyl, hexanoyl, 3-methylpentanoyl and the like.

"$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

"$C_3$–$C_8$ cycloalkyl" represents a saturated hydrocarbon ring structure containing from three to eight carbon atoms. Typical $C_3$–$C_8$ cycloalkyl groups include cyclopropyl, cyclopentyl, cyclohexyl, cycloheptyl, and the like.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxy-carbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (t-BOC), allyloxycarbonyl and benzyloxycarbonyl. Further examples of groups referred to by the above terms are described by E. Haslam, "Protective Groups in Organic Chemistry", (J. G. W. McOmie, ed., 1973), at Chapter 2; and T. W. Greene and P. G. M. Wuts, "Protective Groups in Organic Synthesis" (1991), at Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxy-benzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, supra, at Chapter 5, and T. W. Greene, et al., supra, at Chapter 5.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$-$C_7$ alkyl).

The compounds used in the method of the present invention have multiple asymmetric centers. As a consequence of these chiral centers, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

In addition to the (R)-(S) system, the older D-L system is also used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

As noted supra, this invention includes the pharmaceutically acceptable salts of the compounds defined by Formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses the pharmaceutically acceptable solvates of the compounds of Formulas I. Many of the Formula I compounds can combine with solvents such as water, methanol, ethanol and acetonitrile to form pharmaceutically acceptable solvates such as the corresponding hydrate, methanolate, ethanolate and acetonitrilate.

The especially preferred methods of this invention are those methods employing compounds wherein a) $R^2$ is substituted or unsubstituted 2- or 3-indolyl, phenyl, or naphthyl;

b) n is 1;

c) $R^1$ is hydrogen, phenyl, substituted phenyl, piperidinyl, substituted piperidinyl, piperazinyl, substituted piperazinyl, pyrrolidinyl, pyridyl, benzoyl, or morpholinyl;

d) $R^3$ is phenyl, substituted phenyl, $C_3$–$C_8$ cycloalkyl, substituted $C_3$–$C_8$ cycloalkyl, naphthyl or substituted naphthyl; and e) $R^8$ is hydrogen or methyl.

A most preferred group of compounds used in the methods of this invention are those of Formula I wherein $R^2$ is optionally substituted indolyl, $R^1$ is substituted piperidinyl or substituted piperazinyl, and $R^8$ is hydrogen or methyl. Another preferred group of compounds used in the methods of this invention are those of Formula I wherein $R^2$ is substituted phenyl, $R^1$ is optionally substituted phenyl, substituted piperidinyl or substituted piperazinyl, and $R^3$ is phenyl or substituted phenyl.

The compounds of the present invention can be prepared by a variety of procedures well known to those of ordinary skill in the art. The particular order of steps required to produce the compounds of Formula I is dependent upon the particular compound being synthesized, the starting compound, and the relative lability of the substituted moieties.

An especially preferred process for preparing the compounds of Formula I is by the cyclization of a compound of Formula II.

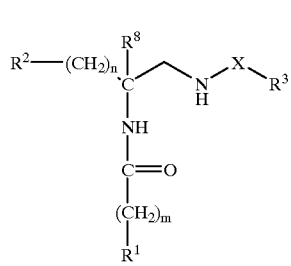

II

A preferred method of cyclizing a compound of Formula II employs heating a solution containing the compound of Formula II in a non-reactive solvent. This dehydration reaction is preferably performed in a solvent having a suitably high boiling point, such as 1,2-dichlorobenzene.

The compounds of Formula II may be prepared by a variety of methods known to those of skill in the art. One such synthesis scheme is shown in the series of reactions depicted in Scheme I, infra.

Scheme I

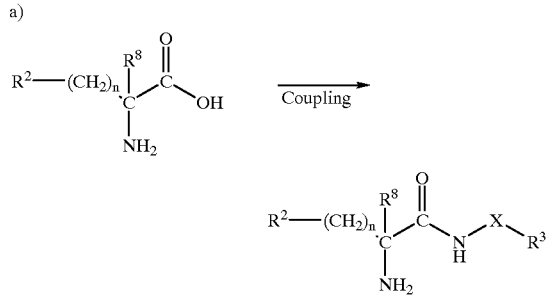

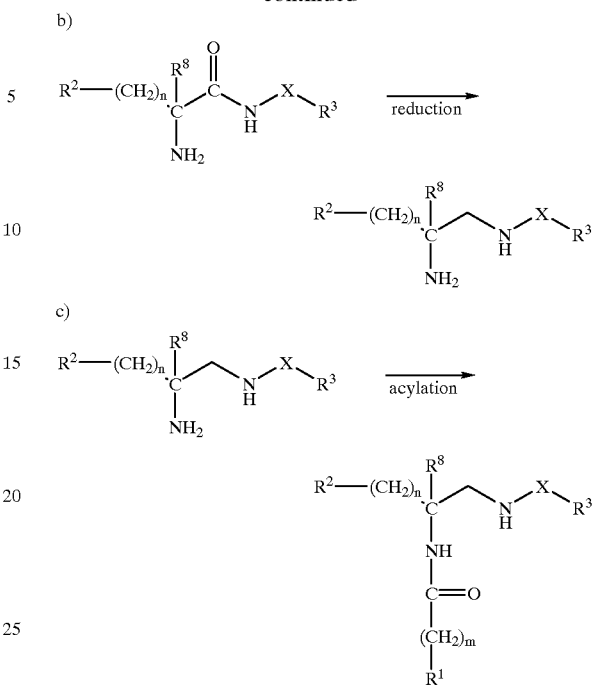

Another preferred method of synthesizing a compound of Formula I is by reacting a compound of Formula III

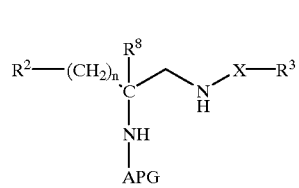

III where APG is an acid-labile amino protecting group, with a carboxylic acid of Formula IV.

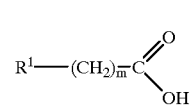

IV

An especially preferred such acid is formic acid. The reaction of a compound of Formula III with a compound of Formula IV results in the formation of an intermediate of Formula V

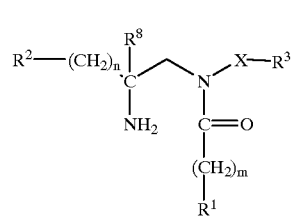

V which may be isolated, but more preferably is not. The conversion of a compound of Formula III to a compound of Formula I proceeds most readily at temperatures greater than 20° C., more preferably at temperatures greater than 50° C.

The reaction is performed in a non-reactive solvent which has a sufficiently high boiling temperature.

If it is desired to isolate the intermediate of Formula V, the reaction is performed at low temperature, preferably at reaction temperatures lower than 10° C., more preferably at temperatures below 0° C.

The compounds of Formula III may be prepared by a variety of methods known to those of skill in the art. One such synthesis scheme is depicted in Scheme II, infra.

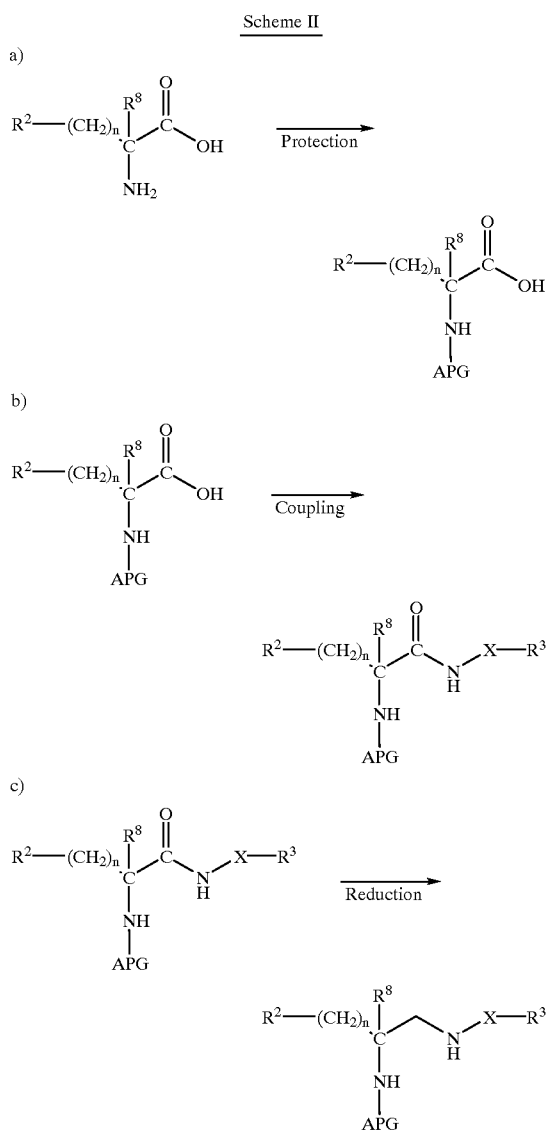

The coupling of the substituted amine can be performed by many means known in the art, the particular methods employed being dependent upon the particular compound used as the starting material and the type of substituted amine used in the coupling reaction. These coupling reactions frequently employ commonly used coupling reagents such as 1,1-carbonyl diimidazole, dicyclohexylcarbodiimide, diethyl azodicarboxylate, 1-hydroxybenzotriazole, alkyl chloroformate and triethylamine, phenyldichlorophosphate, and chlorosulfonyl isocyanate. Examples of these methods are described infra.

The intermediate amides are reduced to amines using procedures well known in the art. These reductions can be performed using lithium aluminum hydride as well as by use of many other different aluminum-based hydrides. An especially preferred reagent employed in this reduction is RED-AL®, which is the tradename of a 3.4 M solution of sodium bis(2-methoxyethoxy)aluminum hydride in toluene. Alternatively, the amides can be reduced by catalytic hydrogenation, though high temperatures and pressures are usually required for this. Sodium borohydride in combination with other reagents may be used to reduce the amide. Borane complexes, such as a borane dimethylsulfide complex, are especially useful in this reduction reaction.

The next step in Scheme I is the selective acylation of the primary amine using standard methods. Because of the higher steric demand of the secondary amine, the primary amine is readily available for selective substitution.

This acylation can be done using any of a large number of techniques regularly employed by those skilled in organic chemistry. One such reaction scheme is a substitution using an anhydride such as acetic anhydride. Another reaction scheme often employed to acylate a primary amine employs a carboxylic acid preferably with an activating agent. An amino-de-alkoxylation type of reaction uses esters as a means of acylating the primary amine. Activated esters which are attenuated to provide enhanced selectivity are very efficient acylating agents. One preferred such activated ester is p-nitrophenyl ester, such as p-nitrophenyl acetate.

Primary amines can also be acylated using amides to perform what is essentially an exchange reaction. This reaction is usually carried out with the salt of the amine. Boron trifluoride, usually in the form of a boron trifluoride diethyl ether complex, is frequently added to this reaction to complex with the leaving ammonia.

In order to preferentially prepare one optical isomer over its enantiomer, the skilled practitioner can proceed by one of two routes. The practitioner may first prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active salt or base. These diastereomers can then be separated using differential solubility, fractional crystallization, chromatography, or like methods. Further details regarding resolution of enantiomeric mixtures can be found in J. Jacques, et al., "Enantiomers, Racemates, and Resolutions", (1991).

In addition to the schemes described above, the practitioner of this invention may also choose an enantiospecific protocol for the preparation of the compounds of Formula I. Such a protocol employs a synthetic reaction design which maintains the chiral center present in the starting material in a desired orientation. These reaction schemes usually produce compounds in which greater than 95 percent of the title product is the desired enantiomer.

Typical reaction conditions for reach of these reactions are described in the preparations and examples infra.

Preparation 1
Preparation of (RS)-1-phenyl-1-(tritylamino)-[N-(2-methoxybenzyl)acetylamino]ethane To a stirring solution of α-aminophenylacetic acid (15.0 g, 99.2 mmol) in 430 ml of methylene chloride was added trimethylsilyl chloride (13.8 ml, 109.12 mmol) dropwise. The resulting mixture was stirred for about ninety minutes, followed by the dropwise addition of triethylamine (30.4 ml, 218.24 mmol). The resulting mixture was then stirred for about thirty minutes after which trityl chloride (30.4 g, 109.12 mmol), dissolved in 50 ml of methylene chloride, was added. The progress of the reaction was monitored by thin layer chromatography.

After the reaction mixture was stirred overnight, the mixture was concentrated in vacuo. The concentrate was then partitioned between 5% citric acid and a 1:1 mixture of ethyl acetate and dietyl ether. The aqueous fraction was then extracted with a 1:1 mixture of ethyl acetate and diethyl ether.

The organic fractions were then combined, washed twice with brine, and then dried over sodium sulfate. The solvents were removed in vacuo and the residue was then dissolved in boiling ethyl acetate and then filtered. The solvents were again removed in vacuo and the resulting α-(tritylamino) phenylacetic acid was recrystallized from boiling ethyl acetate with hexanes added. (Yield: 30.82 g, 79%).

To a stirring solution of α-(tritylamino)phenylacetic acid (19.32 g, 49 mmol) in 650 ml of tetrahydrofuran, 2-methoxybenzylamine (6.72 ml, 49 mmol) was added dropwise, followed by the addition of hydroxybenztriazole hydrate (6.62 g, 49 mmol) and triethylamine (6.83 ml, 49 mmol). The resulting mixture was cooled to 0° C. and then 1-(3-dimethylaminopropyl)-3 -ethylcarbodiimide hydrochloride (9.39 g, 49 mmol) was added, followed by the addition of 400 ml of tetrahydrofuran.

The resulting solution was warmed to room temperature. The progress of the reaction was monitored by thin layer chromatography. After the solution was stirred overnight, the solvents were removed in vacuo. The residue was then dissolved in methylene chloride, washed twice with sodium carbonate, followed by two washings with brine. The organic fraction was then dried over sodium sulfate, and the solvents were removed in vacuo. The resulting intermediate, N-(2-methoxybenzyl)-1-phenyl-1-tritylamino-acetamide (18.81 g, 75%) was recrystallized from boiling ethyl acetate/hexanes.

The N-(2-methoxybenzyl)-1-phenyl-1-(tritylamino) acetamide (18.85 g, 36.6 mmol) was dissolved in 120 ml of tetrahydrofuran and then brought to reflux. RED-AL® [a 3.4 M solution of sodium bis(2-methoxyethoxy)aluminum hydride in toluene] (48 ml, 164.7 mmol) was dissolved in 120 ml of tetrahydrofuran and then added dropwise to the N-(2-methoxybenzyl)-1-phenyl-1-tritylamino-acetamide/tetrahydrofuran solution. The solution was refluxed and the progress of the reaction was monitored by thin layer chromatography.

After the solution was refluxed overnight, the reaction solution was then cooled to room temperature and the reaction was quenched with a saturated Rochelle's salt solution. The resulting mixture was then extracted with ethyl acetate.

The organic fraction was then washed twice with sodium carbonate, twice with brine, and then dried over sodium sulfate. The solvents were then removed in vacuo to yield the intermediate N-(2-methoxybenzyl)-1-phenyi-1-(tritylamino)ethylamine (17.3 g, 95%).

The N-(2-methoxybenzyl)-1-phenyl-1-(tritylamino) ethylamine (16.87 g, 33.8 mmol) was then dissolved in 100 ml of tetrahydrofuran. The resulting solution was cooled to 0° C. and then triethylamine (5.65 ml, 40.6 mmol) was added, followed the addition of acetic anhydride (3.8 ml, 40.6 mmol).

The reaction mixture was then warmed to room temperature and then stirred overnight. The progress of the reaction was monitored by thin layer chromatography. The solvents were then removed in vacuo and the residue was disolved in methylene chloride, washed twice with water, then twice with brine, and then dried over sodium sulfate. The solvents were then removed in vacuc and the residue was washed with boiling diethyl ether to yield the intermediate 1-phenyl-1-(tritylamino)-[N-(2-methoxybenzyl)acetylamino]ethane (18.27 g, 70%).

FDMS 540 (M$^+$).

$^1$H NMR (CDCl$_3$) δ2:1 mixture of amide rotamers 1.9 (s, ⅔·3H), 1.96 (s, ⅓·3H), 2.93 (m, 1H), 3.05 (m, 1H), 3.67 (s, ⅔·3H), 3.75 (s, ⅓·3H) , 3.75 (m, 1H) , 3.93 (d, J=18 Hz, 2H), 4.21 (ABq J=14 Hz, Δv=21 Hz, 1H), 6.66–6.90 (m, 3H), 6.90–7.35 (m, 15H), 7.35–7.55 (m, 6H)

Analysis for $C_{37}H_{36}N_2O_2$:
  Theory: C, 82.19; H, 6.71; N, 5.18.
  Found: C, 82.37; H, 6.69; N, 5.03.

Preparation 2
(RS)-2-amino-2-methyl-1-[N-(2-methoxybenzyl)amino]-3-(1H-indol-3-yl)propane In a 500 ml round-bottom flask under a nitrogen atmosphere, α-methyltryptophan (5.0 g, 22.9 mmol) was slurried in 300 ml of dry tetrahydrofuran. While stirring the reaction mixture 2-methoxybenzylamine (3 ml, 22.9 mmol) was added, followed by the addition of hydroxybenztriazole hydrate (3.15 g, 22.9 mmol) and triethylamine (3.25 ml, 22.9 mmol). The resulting mixture was cooled to 0° C. and then 1-(3-dimethylaminopropyl)-3-ethylcarbodiimide hydrochloride (4.5 g, 22.9 mmol) was added.

The reaction mixture was then slowly warmed to room temperature and was stirred while the progress of the reaction was monitored by thin layer chromatography. After stirring overnight, the reaction mixture was concentrated in vacuo, dissolved in ethyl acetate, and then washed twice with a saturated sodium bicarbonate solution, followed by two washings with brine. The organic fraction was then dried over sodium sulfate and the solvents were removed in vacuo. The desired intermediate, N-(2-methoxybenzyl)-2-methyl-2-amino-1-(1H-indol-3-yl)-3-propionamide, was further purified by chromatography. (Yield: 4.57 g, 60%).

The N-(2-methoxybenzyl)-2-methyl-2-amino-1-(1H-indol-3-yl)-3-propionamide (2.25 g, 6.68 mmol) was dissolved in 15 ml of tetrahydrofuran under a nitrogen atmosphere. The resulting solution was warmed to 80° C. RED-AL® [a 3.4 M solution of sodium bis(2-methoxyethoxy) aluminum hydride in toluene] (8.8 ml, 30.06 mmol) was dissolved in 3.7 ml of tetrahydrofuran and then added dropwise to the reaction mixture. The solution was then warmed to 80° C. and the progress of the reaction was monitored by thin layer chromatography.

After the solution was maintained at 80° C. for about 23 hours, the reaction solution was then cooled to room temperature and the reaction was quenched with a saturated Rochelle's salt solution. The resulting mixture was then extracted twice with ethyl acetate. The organic fraction was washed twice with brine and then dried over sodium sulfate. The solvents were removed in vacuo. The desired (RS)-2-amino-2-methyl-1-[N-(2-methoxybenzyl)amino]-3-(1H-indol-3-yl)propane was further purified by chromatography (1.3 g, 60%).

FDMS 323 (M$^+$)

$^1$H NMR (CDCl$_3$) δ1.15 (s, 3H), 2.60 (s, 2H), 2.74 (br s, 3H), 2.90 (d, J=8 Hz, 2H), 3.80 (s, 3H), 3.87 (s, 2H), 6.83–6.95 (m, 2H), 7.05–7.30 (m, 5H), 7.36 (d, J=8 Hz, 1H), 7.61 (d, J=8 Hz, 1H), 8.48 (br s, 1H).

Analysis for $C_{20}H_{25}N_3O$:
  Theory: C, 74.27; H, 7.79; N, 12.99.
  Found: C, 75.10; H, 8.03; N, 13.44.

Preparation 3
Preparation of 1-phenyl-2-(tritylamino)-3-[N-(2-methoxybenzyl)acetylamino]propane In a three-neck flask 3-phenyl-2-amino-1-propanoic acid (15 g, 90.7 mmol) was slurried with 400 ml of methylene chloride under a nitrogen atmosphere. Trimethylsilyl chloride (12.67 ml, 99.77 mmol) was added dropwise and the resulting mixture was stirred for about ninety minutes, and then triethylamine (27.8 ml, 199.54 mmol) was added dropwise. The reaction mixture was then stirred for about thirty minutes, after which time trityl chloride (27.8 g, 99.77 mmol), dissolved in 50 ml of methylene chloride, was added. The resulting mixture was then stirred overnight at room temperature.

After stirring overnight the reaction mixture was concentrated in vacuo. The residue was partitioned between a 5% citric acid solution and a 1:1 mixture of ethyl acetate and ether. The aqueous fraction was extracted twice with ethyl acetate/ether. The organic fractions were combined, extracted twice with brine and dried over sodium sulfate. The solvents were removed in vacuo.

The desired intermediate, 3-phenyl-2-tritylamino-1-propanoic acid, was then recrystallized from hot acetonitrile. (Yield: 8.04 g, 22%).

The intermediate prepared supra (23.44 g, 57.5 mmol) was then dissolved in 750 ml of tetrahydrofuran under a nitrogen atmosphere while stirring. To this solution was added 2-methoxybenzylamine (7.9 ml, 57.5 mmol), hydroxybenztriazole hydrate (7.77 g, 57.5 mmol) and triethylamine (8.01 ml, 57.5 mmol). The resulting mixture was cooled to 0° C. and 1-(3-dimethylaminopropyl)-3-ethylcarbodiimide hydrochloride (11.02 g, 57.5 mmol) was added. N,N-Dimethylformamide (500 ml) was added and the solution was warmed to room temperature and then stirred overnight.

The solvents were then removed in vacuo and the residue was dissolved in methylene chloride, then washed twice with a saturated sodium carbonate solution, followed by two washes with brine, and then dried over sodium sulfate. The solvents were removed in vacuo and the product was further purified by chromatography to yield the desired title intermediate, N-(2-methoxybenzyl)-1-phenyl-2-(tritylamino)-3-propionamide.

The N-(2-methoxybenzyl)-1-phenyl-2-(tritylamino)-3-propionamide (19.3 g, 36.6 mmol) was dissolved in 120 ml of tetrahydrofuran under a nitrogen atmosphere. The resulting solution was then heated to reflux. RED-AL® [a 3.4 M solution of sodium bis(2-methoxyethoxy)aluminum hydride in toluene] (48 ml, 164.7 mmol) was dissolved in 3.7 ml of tetrahydrofuran and then added dropwise to the reaction mixture. The solution was then heated and the progress of the reaction was monitored by thin layer chromatography.

After refluxing overnight, the reaction mixture was cooled to room temperature and quenched with a saturated Rochelle's salt solution. The resulting mixture was then extracted twice with ethyl acetate. The organic fractions were combined, washed twice with saturated sodium carbonate, then twice with brine, and then dried over sodium sulfate. The solvents were removed in vacuo to yield 19.41 g (>98%) of the desired 1-phenyl-2-(tritylamino)-3-(2-methoxybenzylamino)propane.

The 1-phenyl-2-(tritylamino)-3-(2-methoxybenzylamino) propane prepared supra was then acetylated by dissolving the intermediate (18.6 g, 36.43 mmol) in 100 ml of tetrahydrofuran and then cooling this solution to 0° C. To this stirring solution under a nitrogen atmosphere triethylamine (6.07 ml, 43.6 mmol) and acetic anhydride (4.11 ml, 43.6 mmol) were added and the reaction mixture was allowed to warm to room temperature.

After the reaction mixture was stirred overnight the mixture was concentrated in vacuo and the residue was redissolved in methylene chloride, and then washed twice with water then twice with brine and then dried over sodium sulfate. The solvents were removed in vacuo. The desired title intermediate was recrystallized from boiling ethyl acetate/hexanes to yield 11.33 grams (56%).
FDMS 554 (M+)
$^1$H NMR (CDCl$_3$) 2:1 mixture of amide rotamers δ1.90 (s, ⅔·3H), 1.95 (s, ⅓·3H), 2.36–2.53 (m, 2H), 2.63 (dd, J=4, 13 Hz, 1H), 3.00 (m, 1H), 3.06–3.23 (m, 2H), 3.66 (s, ⅓·3H), 3.76 (s, ⅔·3H), 3.85 (ABq, J=17 Hz, Δν=110 Hz, ⅔·2H), 4.59 (ABq, J=17 Hz, Δν=100 Hz, ⅓·2H), 6.42 (d, J=7 Hz, 1H), 6.68–6.85 (m, 3H), 6.92–7.05 (m, 2H), 7.05–7.43 (m, 12H), 7.50–7.63 (m, 6H).
Analysis for $C_{28}H_{38}N_2O_2$:
  Theory: C, 82.28; H, 6.90; N, 5.05.
  Found: C, 82.01; H, 6.96; N, 5.25.

Preparation 4

Preparation of (RS)-1-[N-(2-methoxybenzyl)amino]-3-(1H-indol-3-yl)-2-[N-(2-((4-phenyl)piperazin-1-yl)acetyl) amino]propane.

To a solution of N-(t-butoxycarbonyl)tryptophan (46.4 g, 152.6 mmoles) in 500 ml of dioxane was added carbonyl diimidazole (25.4 g, 156 mmoles) in a portionwise manner. The resulting mixture was stirred for about 2.5 hours at room temperature and then stirred at 45° C. for 30 minutes. Next, 2-methoxybenzylamine (20.7 ml, 158.7 mmoles) was added and the reaction mixture was then stirred for 16 hours at room temperature.

The dioxane was removed under reduced pressure. The product was partitioned between ethyl acetate and water and was washed successively with 1 N hydrochloric acid, saturated sodium bicarbonate solution, water, and brine, followed by drying over sodium sulfate and removal of the solvent. Final crystallization from methanol yielded 52.2 g of 2-t-butoxycarbonylamino-3-(1H-indol-3-yl)-N-(2-methoxybenzyl)propanamide as yellow crystals. Yield 80.8%.

To a mixture of the 2-t-butoxycarbonylamino-3-(1H-indol-3-yl)-N-(2-methoxybenzyl)propanamide prepared supra (25.1 g, 59.2 mmoles) and anisole (12 ml, 110.4 mmoles) at 0° C. was added dropwise an aqueous solution of trifluoroacetic acid (118 ml, 1.53 moles) in 50 ml of water. This mixture was stirred for one hour at 0° C., followed by stirring for about 2.5 hours at ambient temperature. The mixture was then refrigerated for about 16 hours.

The volatiles were removed under reduced pressure. The product was partitioned between ethyl acetate and saturated sodium bicarbonate solution and was then washed with water followed by brine and then dried over sodium sulfate. The solvents were removed in vacuo. Recrystallization from a 1:1 diethyl ether/cyclohexane solution yielded 18.0 g (94.2%) of 2-amino-3-(1H-indol-3-yl)-N-(2-methoxybenzyl)propanamide as an off-white powder.

To a refluxing solution of 2-amino-3-(1H-indol-3-yl)-N-(2-methoxybenzyl)propanamide (9.81 g, 30.3 mmoles), prepared as described supra, in 100 ml of anhydrous tetrahydrofuran was added dropwise a 10 M borane-methyl sulfide complex (9.1 ml, 91.0 mmoles). The resulting mixture was refluxed for about 2 hours. The mixture was cooled to room temperature and the excess borane was quenched by the dropwise addition of 160 ml of methanol. The resulting mixture was refluxed for 15 minutes and the methanol was removed under reduced pressure.

The residue was dissolved in a saturated methanol solution of hydrochloric acid (250 ml) and the solution refluxed for about 1 hour. The methanol was removed in vacuo and the product was isolated by the addition of 5 N sodium hydroxide followed by extraction with diethyl ether. The product was then dried over sodium sulfate. The solvents were removed in vacuo. Flash chromatography (silica gel, eluting with methanol:methylene chloride:ammonium hydroxide, 10:100:0.5) provided 7.1 g of a mixture of 2-amino-3-(1H-indol-3-yl)-1-[N-(2-methoxybenzyl)amino] propane (75%) and its indoline derivative (25%) as an amber oil.

A mixture of 2-((4-phenyl)piperazin-1-yl)acetic acid, sodium salt (1.64 g, 6.8 mmoles) and triethylamine hydrobromide (1.24 g, 6.8 mmoles) in 35 ml of anhydrous dimethylformamide was heated to 50° C. and remained at that temperature for about 35 minutes. The mixture was allowed to cool to room temperature. 1,1-Carbonyl diimidazole (1.05 g, 6.5 mmoles) and 10 ml of anhydrous dimethylformamide were added to the mixture. The resulting mixture was stirred for about 3 hours at room temperature.

A solution of the 2-amino-3-(1H-indol-3-yl)-1-[N-(2-methoxybenzyl)amino]propane (75%) and the indoline derivative (25%) prepared supra, dissolved in 10 ml of anhydrous dimethylformamide was added to the previous reaction mixture. The resulting mixture was stirred for about 16 hours at room temperature. The dimethylformamide was removed under reduced pressure.

The title product and its indoline derivative were partitioned between ethyl acetate and water and then washed with brine, and dried over sodium sulfate. The solvents were removed in vacuo. This process yielded 3.2 g of a mixture of the title compound and its indoline derivative as a yellow oil. These two compounds were then separated using high performance liquid chromatography using a reverse phase column followed by a silica gel column to give the title product (5.2 % yield) as a yellow foam.
MS 512 ($M^+1^+$)
$^1$H NMR: (CDCl$_3$) δ2.30–2.43 (m, 2H), 2.43–2.54 (m, 2H), 2.70–3.10 (m, 11H), 3.82 (S, 3H), 3.84 (m, 2H), 4.44 (m, 1H), 6.74–6.94 (m, 6H), 7.04 (m, 1H), 7.07–7.36 (m, 7H) 7.64 (d, J=8 Hz, 1H), 8.09 (br s, 1H)
Analysis of C$_{31}$H$_{37}$N$_5$O$_2$:
  Theory: C, 72.77; H, 7.29; N, 13.69.
  Found: C, 72.49; H, 7.33; N, 13.90.
The following compounds were prepared essentially as described above.

Preparation 5
1-(N-benzylamino)-3-(1H-indol-3-yl)-2-[N-(2-((4-phenyl)piperazin-1-yl)acetyl)amino]propane.
MS 481 ($M^+$).
$^1$H NMR: (CDCl$_3$) δ2.28 (m, 1H), 2.32–2.45 (m, 2H), 2.45–2.61 (m, 2H), 2.73 (m, 1H), 2.79–3.15 (m, 8H), 3.21 (m, 1H), 3.96 (ABq, J=8 Hz, Δν=20 Hz, 2H), 4.50 (m, 1H), 6.78–6.99 (m, 3H), 7.04 (m, 1H), 7.10–7.59 (m, 11H), 7.66 (d, J=8 Hz, 1H), 8.10 (br s, 1H).
Analysis of C$_{30}$H$_{35}$N$_5$O:
  Theory: C, 74.81; H, 7.32; N, 14.54.
  Found: C, 74.83; H, 7.38; N, 14.67.

Preparation 6
1-[N-(2-chlorobenzyl)amino]-3-(1H-indol-3-yl)-2-[N-(2-((4-phenyl)piperazin-1-yl)acetyl)amino]propane.
MS (M+) 515, 517.
$^1$H NMR: (DMSO-d$_6$) δ2.33–2.50 (m, 4H), 2.56–2.75 (m, 2H), 2.75–3.09 (m,8H), 3.20 (m, 1H), 4.78 (s, 2H), 5.21 (m, 1H), 6.78 (t, J=8 Hz, 1H), 6.88 (d, J=8 Hz, 2H), 6.98 (t, J=8 Hz, 1H), 7.06 (t, J=8 Hz, 1H), 7.13 (m, 1H), 7.13–7.31 (m, 4H), 7.34 (d, J=7 Hz, 1H), 7.39 (dd, J=2, 6 Hz, 1H), 7.50 (dd, J=2, 7 Hz, 1H), 7.55 (d, J=8 Hz, 1H), 7.61 (d, J=7 Hz, 1H), 10.81 (br s, 1H)

Preparation 7
1-[N-(2-trifluoromethylbenzyl)amino]-3-(1H-indol-3-yl)-2-[N-(2-((4-phenyl)piperazin-1-yl)acetyl)amino]propane.
MS 549 (M+);
Exact Mass FAB
  Theory: 550.2794.
  Found: 550.2801.
$^1$H NMR: (CDCl$_3$) δ2.12 (m, 1H), 2.36–2.44 (m, 2H), 2.44–2.60 (m, 2H), 2.77–3.09 (m, 10H), 4.02 (s, 2H), 4.50 (m, 1H), 6.73–7.00 (m, 3H), 7.00–7.56 (m, 9H, 7.56–7.85 (m, 3H), 8.16 (br s, 1H)

Preparation 8
(RR) 1-[N-(1-methyl-2-phenylethyl)amino]-3-(1H-indol-3-yl)-2-[N-[2-[1-[4-(1-piperidinyl)piperidinyl]acetyl]]amino]propane.
MS 501 (M$^+$).
$^1$H NMR (DMSO d$_6$) δ1.23 (d, J=6 Hz, 3H), 1.12–1.70 (m, 11H), 1.89–2.01 (m, 2H), 2.01–2.17 (m, 2H), 2.23–2.43 (m, 5H), 2.52 (m, 1H), 2.72 (m, 1H), 2.75 (ABq, J=15 Hz, Δν=30 Hz, 2H), 2.83 (dd, J=8, 14 Hz, 1H), 2.95 (dd, J=6, 14 Hz, 1H), 3.66 (q, J=6 Hz, 1H), 4.06 (m, 1H), 6.95 (t, J=8 Hz, 1H), 6.99–7.10 (m, 2H), 7.10–7.41 (m, 6H), 7.49 (d, J=9 Hz, 1H), 7.56 (d, J=8 Hz, 1H), 10.78 (br s, 1H)
Analysis of C$_{31}$H$_{43}$N$_5$O:
  Theory: C, 74.21; H, 8.64; N, 13.96.
  Found: C, 73.93; H, 8.65; N, 13.89.

Preparation 9
(R) 1-[N-(2-methoxybenzyl)amino]-3-(1H-indol-3-yl)-2-[N-(2-((4-phenyl)piperazin-1-yl)acetyl)amino]propane.
MS 512 ($M^+1^+$)
$^1$H NMR: (CDCl$_3$) δ2.30–2.43 (m, 2H), 2.43–2.56 (m, 2H), 2.64–3.12 (m, 11H), 3.59–3.93 (m, 2H), 3.82 (s, 3H), 4.43 (m, 1H), 6.68–6.96 (m, 6H), 7.03 (m, 1H), 7.07–7.45 (m, 7H), 7.66 (d, J=8 Hz, 1H), 8.04 (br s, 1H)
Analysis of C$_{31}$H$_{37}$N$_5$O$_2$:
  Theory: C, 72.77; H, 7.29; N, 13.69.
  Found: C, 72.58; H, 7.39; N, 13.65.

Preparation 10
(S) 1-[N-(2-methoxybenzyl)amino]-3-(1H-indol-3-yl)-2-[N-(2-((4-phenyl)piperazin-1-yl)acetyl)amino]propane.
MS 512 ($M^+1^+$)
$^1$H NMR: (CDCl$_3$) δ2.22–2.38 (m, 2H), 2.38–2.50 (m, 2H), 2.50–3.27 (m, 11H), 3.84 (s, 3H), 3.96 (ABq, J=13 Hz, Δν=21 Hz, 2H), 4.27 (m, 1H), 6.75–6.97 (m, 6H), 6.99–7.39 (m, 8H), 7.63 (d, J=8 Hz, 1H), 8.12 (br s, 1H)
Analysis of C$_{31}$H$_{37}$N$_5$O$_2$:
  Theory: C, 72.77; H, 7.29; N, 13.69.
  Found: C, 73.01; H, 7.50; N, 13.69.

Preparation 11
1-[N-(3-methoxybenzyl)amino]-3-(1H-indol-3-yl)-2-[N-(2-((4-phenyl)piperazin-1-yl)acetyl)amino]propane.
MS 511 (M$^+$)
$^1$H NMR: (CDCl$_3$) δ7:3 mixture of amide rotamers 2.20–3.74 (m, 14H), 3.74 (m, 1H), 3.76 (s, ³⁄₁₀·3H), 3.80 (s, ⁷⁄₁₀·3H), 4.13 (ABq, J=14 Hz, Δν=50 Hz, ⁷⁄₁₀·2H), 4.67 (m, 1H), 4.70 (ABq, J=14 Hz, Δν=160 Hz, ³⁄₁₀·2H), 6.82–7.00 (m, 6H), 7.00–7.45 (m, 8H), 7.59 (d, J=8 Hz, 1H), 8.10 (br s, ³⁄₁₀·1H), 8.41 (br s, ⁷⁄₁₀·1H)
Analysis of C$_{31}$H$_{37}$N$_5$O$_2$:
  Theory: C, 72.77; H, 7.29; N, 13.69.
  Found: C, 73.00; H, 7.19; N, 13.91.

Preparation 12
1-[N-(4-methoxybenzyl)amino]-3-(1H-indol-3-yl)-2-[N-(2-((4-phenyl)piperazin-1-yl)acetyl)amino]propane.

MS 511 (M+).
¹H NMR (CDCl₃) δ2.21–2.63 (m, 4H), 2.63–2.90 (m, 4H), 2.90–3.40 (m, 6H), 3.75 (m, 1H), 3.77 (s, 3H), 4.04 (ABq, J=12 Hz, Δv=54 Hz, 2H), 4.64 (m, 1H), 6.83–6.95 (m, 5H), 6.95–7.48 (m, 8H), 7.50–7.75 (m, 2H), 8,23 (br s, 1H)
Analysis of $C_{31}H_{37}N_{5O2}$:
  Theory: C, 72.77; H, 7.29; N, 13.69.
  Found: C, 72.58; H, 7.35; N, 13.70.

Preparation 13
(R) 1-[N-(2-methoxybenzyl)amino]-3-(1H-indol-3-yl)-2-[N-(2-((4-piperidin-1-yl)piperidin-1-yl)acetyl)amino]propane.
MS 517 (M+).
¹H NMR (CDCl₃) δ1.10–2.18 (m, 12H), 2.18–3.18 (m, 14H), 3.61–3.95 (m, 2H), 3.93 (s, 3H), 4.36 (m, 1H), 6.76–6.96 (m, 3H), 7.04–7.44 (m, 5H), 7.42 (d, J=8 Hz, 1H), 7.65 (d, J=8 Hz, 1H), 9.13 (br s, 1H)
Analysis of $C_{31}H_{43}N_5O_2$:
  Theory: C, 71.92; H, 8.37; N, 13.53.
  Found: C, 71.69; H, 8.25; N, 13.26.

Preparation 14
(S) 1-[N-(2-methoxybenzyl)amino]-3-(1H-indol-3-yl)-2-[N-[2-[1-[4-(1-piperidinyl)piperidinyl]acetyl]]amino]propane.
MS 517 (M+).
¹H NMR (CDCl₃) δ1.13–2.18 (m, 12H), 2.18–3.33 (m, 14H) 3.61–3.96 (m, 2H), 3.85 (s, 3H), 4.36 (m, 1H), 6.80–6.97 (m, 3H), 6.97–7.36 (m, 6H), 7.44 (d, J=8 Hz, 1H), 9.60 (br s, 1H)
Analysis of $C_{31}H_{43}N_5O_2$:
  Theory: C, 71.92; H, 8.37; N, 13.53.
  Found: C, 71.91; H, 8.25; N, 13.42.

Preparation 15
(RS) 1-[N-(1-methyl-2-phenylethyl)amino]-3-(1H-indol-3-yl)-2-[N-[2-[1-[4-(1-piperidinyl)piperidinyl]acetyl]]amino]propane.
MS 501 (M+).
¹H NMR (CDCl₃) δ1.32 (d, J=7 Hz, 3H) , 1.15–1.91 (m, 11H) 1.91–2.23 (m, 3H), 2.30–2.60 (m, 6H), 2.65 (dd, J=6, 14 Hz, 1H), 2.72–2.94 (m, 4H), 3.01 (dd, J=6, 14 Hz, 1H), 3.72 (q, J=7 Hz, 1H), 4.35 (m, 1H), 6.95 (d, J=2 Hz, 1H), 7.03–7.42 (m, 9H), 7.64 (d, J=8 Hz, 1H), 8.08 (br s, 1H)
Analysis of $C_{31}H_{43}N_5O$:
  Theory: C, 74.21; H, 8.64; N, 13.96.
  Found: C, 74.50; H, 8.49; N, 13.94.

Preparation 16
1-[N-(2-methoxybenzyl)amino]-3-(1H-indol-3-yl)-2-[(N-acetyl)amino]propane.
MS 351 (M+).
1H NMR (CDCl₃) δ1.97 (s, 3H), 2.38 (m, 1H), 2.73 (dd, J=6, 12 Hz, 1H), 2.82 (dd, J=6, 12 Hz, 1H), 2.97 (dd, J=8, 14 Hz, 1H), 3.10 (dd, J=6, 14 Hz, 1H), 3.75–3.94 (m, 2H), 3.82 (s, 3H), 4.42 (m, 1H), 6.34 (br d, J=8 Hz, 1H), 6.77–6.95 (m, 2H), 7.01 (d, J=2 Hz, 1H), 7.07–7.33 (m, 4H), 7.37 (d, J=8 Hz, 1H), 7.68 (d, J=8 Hz, 1H), 8.13 (br s, 1H)
Analysis of $C_{21}H_{25}N_3O_2$:
  Theory: C, 71.77; H, 7.17; N, 11.96.
  Found: C, 71.48; H, 6.90; N, 12.09.

EXAMPLE 1
Preparation of 1-(2-methoxybenzyl)-2-methyl-4-phenyl-2-imidazoline

The 1-phenyl-1-(tritylamino)-2-[N-(2-methoxybenzyl) acetylamino]ethane, prepared as described in Preparation 1, supra, was detritylated and cyclized by dissolving the intermediate (8.0 g, 14.8 mmol) in 250 ml of methylene chloride and cooling this solution to 0° C. under a nitrogen atmosphere. Formic acid (5.7 ml, 148 mmol) was then added and the reaction mixture was warmed to room temperature and then stirred for 2.5 hours. The progress of the reaction was monitored by thin layer chromatography.

The reaction mixture was then concentrated in vacuo, and was partitioned between diethyl ether and 1N hydrochloric acid. The aqueous fraction was then washed twice with diethyl ether. The resulting aqueous fraction was then basified to pH 12.0, then extracted four times with methylene chloride. The methylene chloride fractions were combined and dried over sodium sulfate. The solvents were removed in vacuo. The desired title product was then further purified by chromatography to yield the desired title product as an oil (50 mg, 1.2%).
FDMS 281 (M+1).
¹H NMR (CDCl₃) δ2.34 (s, 3H), 3.28 (m, 1H), 3.82 (m, 1H) 3.86 (s, 3H), 4.42 (ABq, J=15 Hz, Δυ=33 Hz, 2H), 5.10 (m, 1H), 6.80–7.10 (m, 2H), 7.10–7.50 (m, 7H).
Analysis of $C_{18}H_{20}N_2O$:
  Theory: C, 77.11; H, 7.19; N, 9.99.
  Found: C, 77.23; H, 7.01; N, 9.69.

EXAMPLE 2
Preparation of 1-(2-methoxybenzyl)-2-[(4-phenyl-1-piperazinyl)methyl]-4-(1H-indol-3-ylmethyl)-2-imidazoline A stirring solution of (RS) 1-[N-(2-methoxybenzyl) amino]-3-(1H-indol-3-yl)-2-[N-(2-((4-phenyl)piperazin-1-yl)acetyl)amino]propane (50 mg, 0.098 mmol), prepared as described in Preparation 4, supra, dissolved in 6 ml of 1,2-dichlorobenzene was heated to reflux under a nitrogen atmosphere. The solution was allowed to reflux overnight. The progress of the reaction was monitored by thin layer chromatography. The solution was then refluxed for an additional eight hours. The desired title product was then purified by chromatography. (Yield: 40.0 mg, 83%).
FDMS 494 (M+1)
¹H NMR (DMSO) δ2.63 (dd, J=6, 10HZ, 1H), 2.82–3.04 (m, 6H), 3.04–3.38 (m, 7H), 3.70 (s, 3H), 4.13 (m, 1H), 4.34 (m, 2H), 6.65–7.06 (m, 10H), 7.06–7.23 (m, 2H), 7.27 (d, J=8 Hz, 1H), 7.43 (d, J=8 Hz, 1H), 10.75 (s, 1H).
Analysis for $C_{31}H_{35}N_5O$:
  Theory: C, 75.43; H, 7.15; N, 14.19.
  Found: C, 75.15; H, 7.21; N, 14.06.

EXAMPLE 3
Preparation of 1-(2-methoxybenzyl)-2,4-dimethyl-4-(1H-indol-3-ylmethyl)-2-imidazoline A solution of (RS) 2-amino-2-methyl-1-[N-(2-methoxybenzyl)amino]-3-(1H-indol-3-yl)propane (0.100 g, 0.309 mmol) in 1.5 ml of tetrahydrofuran was cooled to 0° C. To this cooled, stirring solution was added Hunig's base (44 m, 0.34 mmol) followed by the dropwise addition of p-nitrophenylacetate (56 mg, 0.309 mmol), which had previously been dissolved in 1.5 ml of tetrahydrofuran. The reaction mixture was then stirred at 0° C. for about 120 hours and then allowed to warm to room temperature. The progress of the reaction was monitored by thin layer chromatography.

The reaction mixture was concentrated in vacuo, dissolved in ethyl acetate, and then extracted twice with 1N hydrochloric acid. The aqueous fraction was basified to pH 12.0 with 1N sodium hydroxide and then extracted twice with ethyl acetate. The organic fractions were combined and concentrated in vacuo to yield the title product as an oil (10 mg, 9.3%) (99% pure as determined by high performance liquid chromatography).

FDMS 348 (M$^{+1}$)
$^1$H NMR (CDCl$_3$) δ1.43 (s, 3H), 2.08 (s, 3H), 2.85–3.13 (m, 3H), 3.42 (d, J=10 Hz, 1H), 3.73 (s, 3H), 4.00–4.16 (m, 2H), 6.64–6.90 (m, 3H), 7.00–7.36 (m, 4H), 7.39 (d, J=8 Hz, 1H), 7.51 (d, J=8 Hz, 1H), 8.60 (br s, 1H).
Analysis for C$_{22}$H$_{25}$N$_3$O·0.33 EtOAc:
Theory: C, 74.38; H, 7.40; N, 11.16.
Found: C, 74.28; H, 7.17; N, 10.80.

EXAMPLE 4

Preparation of 1-(2-methoxybenzyl)-2-methyl-4-benzyl-2-imidazoline

The intermediate 1-phenyl-2-(tritylamino)-3-[N-(2-methoxybenzyl)acetylamino]propane (8.0 g, 14.4 mmol), prepared as described in Preparation 3, supra, was dissolved in 250 ml of methylene chloride and then cooled to 0° C. under a nitrogen atmosphere. Formic acid (5.5 ml, 144.0 mmol) was then added to the reaction solution and the resulting mixture was then warmed to room temperature. The reaction mixture was then stirred for about 2.5 hours. The progress of the reaction was monitored by thin layer chromatography.

The solvents were removed in vacuo and the residue was partitioned between diethyl ether and 1N hydrochloric acid. The aqueous layer was washed thrice with diethyl ether and then basified to pH 12.0 with 1N sodium hydroxide. The aqueous layer was then extracted four times with methylene chloride. The methylene chloride fractions were combined, and then dried over sodium sulfate. The solvents were removed in vacuo. The desired title product was further purified chromatography to yield 222 mg (5%) of the substituted 2-imidazoline as an oil.
FDMS Exact Mass (M$^+$) 295.181039.
$^1$H NMR (DMSO) δ2.18 (s, 3H), 2.73 (m, 1H), 2.85 (m, 1H), 3.23 (m, 1H), 3.55 (m, 1H), 3.74 (s, 3H), 4.37 (s, 3H), 6.85–6.93 (m, 3H), 6.93–7.07 (m, 2H), 7.07–7.37 (m, 4H).
Analysis for C$_{19}$H$_{22}$N$_2$O:
Theory: C, 77.52; H, 7.53; N, 9.52.
Found: C, 76.18; H, 7.47; N, 9.96.

The biological activity of the compounds of the present invention was evaluated employing an initial screening assay which rapidly and accurately measured the binding of the tested compound to known NK-1 and NK-2 receptor sites. Assays useful for evaluating tachykinin receptor antagonists are well known in the art. See, e.g., J. Jukic, et al., *Life Sciences,* 49:1463–1469 (1991); N. Kucharczyk, et al., *Journal of Medicinal Chemistry,* 36:1654–1661 (1993); N. Rouissi, et al., *Biochemical and Bioohysical Research Communications,* 176:894–901 (1991).

NK-1 Receptor Binding Assay

Radioreceptor binding assays were performed using a derivative of a previously published protocol. D. G. Payan, et al., *Journal of Immunology,* 133:3260–3265 (1984). In this assay an aliquot of IM9 cells (1×10$^6$ cells/tube in RPMI 1604 medium supplemented with 10% fetal calf serum) was incubated with 20 pM $^{125}$I-labeled substance P in the presence of increasing competitor concentrations for 45 minutes at 4° C.

The IM9 cell line is a well-characterized cell line which is readily available to the public. See, e.g., *Annals of the New York Academy of Science,* 190: 221–234 (1972); *Nature (London),* 251:443–444 (1974); *Proceedings of the National Academy of Sciences (USA),* 71:84–88 (1974). These cells were routinely cultured in RPMI 1640 supplemented with 50 gg/ml gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

Table I, infra, depicts the results of several such substance P binding assays. Column 1 provides the example number of the test antagonist compound. The second column depicts the results of the competition assays, detailing the concentration of the test compound (in micromolar quantities) which inhibits fifty percent of the binding of substance P (IC$_{50}$). Certain values may represent the average of more than one experiment.

TABLE I

Effectiveness of Compounds as NK-1 Receptor Antagonists

| Example Number | IC$_{50}$ (μM) |
|---|---|
| 1 | 0.18 |
| 2 | 0.12 |
| 3 | 0.56 |
| 4 | 0.14 |

Many of the compounds employed in the methods of the present invention are also effective antagonists of the NK-2 receptor.

NK-2 Receptor Binding Assay

The CHO-hNK-2R cells, a CHO-derived cell line transformed with the human NK-2 receptor, expressing about 400,000 such receptors per cell, were grown in 75 cm$^2$ flasks or roller bottles in minimal essential medium (alpha modification) with 10% fetal bovine serum. The gene sequence of the human NK-2 receptor is given in N. P. Gerard, et al., *Journal of Biological Chemistry,* 65:20455–20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets were washed once using the above procedure. and the final pellets were resuspended in 100–120 ml 50 mM Tris buffer, pH 7.4, and 4 ml aliquots stored frozen at −70° C. The protein concentration of this preparation was 2 mg/ml.

For the receptor binding assay, one 4-ml aliquot of the CHO-hNK-2R membrane preparation was suspended in 40 ml of assay buffer containing 50 mM Tris, pH 7.4, 3 mM manganese chloride, 0.02% bovine serum albumin (BSA) and 4 μg/ml chymostatin. A 200 μl volume of the homogenate (40 μg protein) was used per sample. The radioactive ligand was [$^{125}$I]iodohistidyl-neurokinin A (New England Nuclear, NEX-252), 2200 Ci/mmol. The ligand was prepared in assay buffer at 20 nCi per 100 μl; the final concentration in the assay was 20 pM. Non-specific binding was determined using 1 μM eledoisin. Ten concentrations of eledoisin from 0.1 to 1000 nM were used for a standard concentration-response curve.

All samples and standards were added to the incubation in 10 μl dimethylsulfoxide (DMSO) for screening (single dose) or in 5μl DMSO for IC$_{50}$ determinations. The order of additions for incubation was 190 or 195 μl assay buffer, 200 μl homogenate, 10 or 5 μl sample in DMSO, 100 μl radioactive ligand. The samples were incubated 1 hr at room temperature and then filtered on a cell harvester through filters which had been presoaked for two hours in 50 mN Tris buffer, pH. 7.7, containing 0.5% BSA. The filter was washed 3 times with approximately 3 ml of cold 50 mM Tris buffer, pH 7.7, The filter circles were then punched into 12×75 mn polystyrene tubes and counted in a gamma counter.

Table II, infra, provides a representative sample of the effectiveness as NK-2 receptor antagonists of many of the compounds of Formula I. The first column provides the Example number of the compound tested. The second column provides the amount of compound (in micromolar amounts) necessary to inhibit fifty percent of the binding of neurokinin A ($IC_{50}$). For Example 4 the biological effectiveness of the compound is described as a percent inhibition of neurokinin A binding at a concentration of test compound, in this instance at 10 μM.

TABLE II

Effectiveness of the Compounds of Formula I as
NK-2 Receptor Antagonists

| Example No. | $IC_{50}$ (μM) |
|---|---|
| 1 | 16.0 |
| 2 | 0.47 |
| 3 | 9.1 |
| 4 | 21% at 10 μM |

As the compounds of Formula I are effective tachykinin receptor antagonists, these compounds are of value in the treatment of a wide variety of clinical conditions which are characterized by the presence of an excess of tachykinin. Thus, the invention provides methods for the treatment or prevention of a physiological disorder associated with an excess of tachykinins, which method comprises administering to a mammal in need of said treatment an effective amount of a compound of Formula I or a pharmaceutically acceptable salt, solvate or prodrug thereof. The term "physiological disorder associated with an excess of tachykinins" encompasses those disorders associated with an inappropriate stimulation of tachykinin receptors, regardless of the actual amount of tachykinin present in the locale.

These physiological disorders may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis;

hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites;

addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease, emesis, and irritable bowel syndrome; disorders of bladder function such as bladder detrusor hyper-reflexia and incontinence; artherosclerosis; fibrosing and collagen diseases such as scleroderma and eosinophilic fascioliasis; irritative symptoms of benign prostatic hypertrophy; disorders of blood flow caused by vasodilation and vasospastic diseases such as angina, migraine, and Reynaud's disease; and pain or nociception, for example, that attributable to or associated with any of the foregoing conditions, especially the transmission of pain in migraine. For example the compounds of Formula I may suitably be used in the treatment of disorders of the central nervous system such as anxiety, psychosis, and schizophrenia; neurodegenerative disorders such as Alzheimer's disease and Down's syndrome; respiratory diseases such as bronchospasm and asthma; inflammatory diseases such as inflammatory bowel disease, osteoarthritis and rheumatoid arthritis; adverse immunological disorders such as rejection of transplanted tissues; gastrointestinal disorders and diseases such as disorders associated with the neuronal control of viscera such as ulcerative colitis, Crohn's disease, emesis, and irritable bowel syndrome; incontinence; disorders of blood flow caused by vasodilation; and pain or nociception, for example, that attributable to or associated with any of the foregoing conditions or the transmission of pain in migraine.

The results of several experiments demonstrate that many of the compounds of Formula I are selective tachykinin receptor antagonists. These compounds preferentially bind one tachykinin receptor subtype compared to other such receptors. Such compounds are especially preferred.

For example, NK-1 antagonists are most especially preferred in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, angina pain, and genitourinary tract-related pain including cystitis.

In addition to pain, NK-1 antagonists are especially preferred in the treatment and prevention of urinary incontinence; irritative symptoms of benign prostatic hypertrophy; motility disorders of the gastrointestinal tract, such as irritable bowel syndrome; acute and chronic obstructive airway diseases, such as bronchospasm, bronchopneumonia, asthma, and adult respiratory distress syndrome; artherosclerosis; inflammatory conditions, such as inflammatory bowel disease, ulcerative colitis, Crohn's disease, rheumatoid arthritis, osteoarthritis, neurogenic inflammation, allergies, rhinitis, cough, dermatitis, urticaria, psoriasis, conjunctivitis, emesis, irritation-induced miosis; tissue transplant rejection; plasma extravasation resulting from cytokine chemotherapy and the like; spinal cord trauma; stroke; cerebral stroke (ischemia);

Alzheimer's disease; Parkinson's disease; multiple sclerosis; amyotrophic lateral sclerosis; schizophrenia; anxiety; and depression.

NK-2 antagonists are especially preferred in the treatment of urinary incontinence, bronchospasm, asthma, adult respiratory distress syndrome, motility disorders of the gastrointestinal tract, such as irritable bowel syndrome, and pain.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes pharmaceutical compositions which contain, as the active ingredient, the compounds of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |

-continued

| Ingredient | Quantity (mg/tablet) |
|---|---|
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Examule 8

Capsules, each containing 15 mg of medicament, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
|---|---|
| Active Ingredient | 250.0 mg |
| Isotonic saline | 1000 ml |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
|---|---|
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by prefernce.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

What is claimed is:

1. A compound of the formula

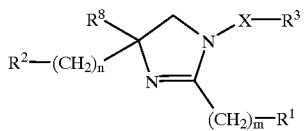

wherein:

m is 0 or 1;

n is 0 or 1;

X is $-(CHR^4)_p-(CHR^6)_q-$, where, p is 0 or 1;

q is 1; and $R^4$ and $R^6$ are independently selected from the group consisting of hydrogen and $C_1-C_3$ alkyl;

$R^2$ is phenyl, 2- or 3-indolyl, 2- or 3-indolinyl, benzothienyl, benzofuranyl, or naphthyl;

any one of which phenyl, 2- or 3-indolyl, 2- or 3-indolinyl, benzothienyl, benzofuranyl, or naphthyl groups is unsubstituted or substituted with one or two moieties independently selected from the group consisting of halo, $C_1-C_3$ alkoxy, trifluoromethyl, $C_1-C_4$ alkyl, phenyl-$C_1-C_3$ alkoxy, and $C_1-C_4$ alkanoyl groups;

$R^1$ is hydrogen, trityl, phenyl, diphenylmethyl, phenoxy, phenylthio, hexamethyleneiminyl, piperazinyl, piperidinyl, pyrrolidinyl, morpholinyl, indolinyl, indolyl, benzothienyl, benzofuranyl, quinolinyl, isoquinolinyl, tetrahydropyridinyl, reduced quinolinyl, reduced isoquinolinyl, phenyl-($C_1-C_6$ alkylidenyl)-, phenyl-($C_1-C_4$ alkoxy)-, quinolinyl-($C_1-C_6$ alkylidenyl)-, isoquinolinyl-($C_1-C_6$ alkylidenyl)-, reduced quinolinyl-($C_1-C_6$ alkylidenyl)-, reduced isoquinolinyl-($C_1-C_6$ alkylidenyl)-, benzoyl-($C_1-C_6$ alkylidenyl)-, $C_1-C_4$ alkyl, or $-NH-CH_2-R^5$;

any one of which $R^1$ groups is unsubstituted or substituted with halo, $C_1-C_4$ alkyl, $C_1-C_4$ alkoxy, trifluoromethyl, amino, $C_1-C_4$ alkylamino, or di($C_1-C_4$ alkyl)amino;

or any one of which $R^1$ groups is unsubstituted or substituted with phenyl, piperazinyl, $C_3-C_8$ cycloalkyl, benzyl, $C_1-C_4$ alkyl, piperidinyl, pyridinyl, pyrimidinyl, $C_2-C_6$ alkanoylamino, pyrrolidinyl, $C_2-C_6$ alkanoyl, or $C_1-C_4$ alkoxycarbonyl;

any one of which phenyl, piperazinyl, $C_3-C_8$ cycloalkyl, benzyl, $C_1-C_4$ alkyl, piperidinyl, pyridinyl, pyrimidinyl, $C_2-C_6$ alkanoylamino, pyrrolidinyl, $C_2-C_6$ alkanoyl, or $C_1-C_4$ alkoxycarbonyl groups is unsubstituted or substituted with halo, $C_1-C_4$ alkyl, $C_1-C_4$ alkoxy, trifluoromethyl, amino, $C_1-C_4$ alkylamino, di($C_1-C_4$ alkyl)amino, or $C_2-C_4$ alkanoylamino;

or $R^1$ is amino, a leaving group, hydrogen, $C_1-C_4$ alkylamino, or di($C_1-C_4$ alkyl)amino;

$R^5$ is pyridyl, anilino-($C_1-C_6$ alkylidenyl)-, or anilinocarbonyl;

$R^8$ is hydrogen or $C_1-C_6$ alkyl; and $R^3$ is phenyl, phenyl-($C_1-C_6$ alkylidenyl)-, $C_3-C_8$ cycloalkyl, $C_5-C_8$ cycloalkenyl, $C_1-C_8$ alkyl, naphthyl, $C_2-C_8$ alkenyl, or hydrogen;

any one of which $R^3$ groups except hydrogen is unsubstituted or substituted with one or two halo, $C_1-C_3$ alkoxy, $C_1-C_3$ alkylthio, nitro, trifluoromethyl, or $C_1-C_3$ alkyl groups;

provided that if $R^2$ is phenyl and $R^8$ is hydrogen, $R^1$ cannot be $C_1-C_4$ alkyl, phenyl, or hydrogen;

or a salt or solvate thereof.

2. A compound as claimed in claim 1 wherein $R^3$ is phenyl, or phenyl-($C_1-C_6$ alkyl)-, any one of which groups is unsubstituted or substituted with one or two chloro, fluoro, trifluoromethyl, methoxy, ethoxy, methyl, or ethyl groups.

3. A compound as claimed in claim 2 wherein $R^2$ is phenyl, 2-indolyl, 3-indolyl, 2-indolinyl, 3-indolinyl, or naphthyl, any one of which groups is unsubstituted or substituted with one or two chloro, fluoro, methyl, ethyl, methoxy, or ethoxy groups.

4. A compound as claimed in claim 3 wherein $R^1$ is hydrogen, phenyl, piperazinyl, piperidinyl, morpholinyl, benzofuranyl, phenyl-($C_1$–$C_4$ alkyl)-, phenyl-($C_1$–$C_4$ alkoxy)-, —NH—$CH_2$—$R^5$, any one of which groups is unsubstituted or substituted.

5. A compound as claimed in claim 4 wherein $R^1$ is hydrogen, 1-(4-phenyl)piperazinyl, 1-(4-cyclohexyl)piperazinyl, 1-(4-phenyl)piperidinyl, 1-(4-cyclohexyl)piperidinyl, 1-(4-isopropyl)piperazinyl, or 1-[4-(1-piperidinyl)]piperidinyl.

6. A pharmaceutical formulation comprising an effective amount of a compound of the formula

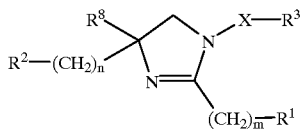

wherein:
m is 0 or 1;
n is 0 or 1;
X is —$(CHR^4)_p$—$(CHR^6)_q$—, where,
p is 0 or 1;
q is 1; and
$R^4$ and $R^6$ are independently selected from the group consisting of hydrogen and $C_1$–$C_3$ alkyl;
$R^2$ is phenyl, 2- or 3-indolyl, 2- or 3-indolinyl, benzothienyl, benzofuranyl, or naphthyl;
any one of which phenyl, 2- or 3-indolyl, 2- or 3-indolinyl, benzothienyl, benzofuranyl, or naphthyl groups is unsubstituted or substituted with one or two moieties independently selected from the group consisting of halo, $C_1$–$C_3$ alkoxy, trifluoromethyl, $C_1$–$C_4$ alkyl, phenyl-$C_1$–$C_3$ alkoxy, and $C_1$–$C_4$ alkanoyl groups;
$R^1$ is hydrogen, trityl, phenyl, diphenylmethyl, phenoxy, phenylthio, hexamethyleneiminyl, piperazinyl, piperidinyl, pyrrolidinyl, morpholinyl, indolinyl, indolyl, benzothienyl, benzofuranyl, quinolinyl, isoquinolinyl, tetrahydropyridinyl, reduced quinolinyl, reduced isoquinolinyl, phenyl-($C_1$–$C_6$ alkylidenyl)-, phenyl-($C_1$–$C_4$ alkoxy)-, quinolinyl-($C_1$–$C_6$ alkylidenyl)-, isoquinolinyl-($C_1$–$C_6$ alkylidenyl)-, reduced quinolinyl-($C_1$–$C_6$ alkylidenyl)-, reduced isoquinolinyl-($C_1$–$C_6$ alkylidenyl)-, benzoyl-($C_1$–$C_6$ alkylidenyl)-, $C_1$–$C_4$ alkyl, or —NH—$CH_2$—$R^5$;
any one of which $R^1$ groups is unsubstituted or substituted with halo, $C_1$–$C_4$ alkyl, $C_1$–$C_4$ alkoxy, trifluoromethyl, amino, $C_1$–$C_4$ alkylamino, or di($C_1$–$C_4$ alkyl)amino;
or any one of which $R^1$ groups is unsubstituted or substituted with phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrrolidinyl, $C_2$–$C_6$ alkanoyl, or $C_1$–$C_4$ alkoxycarbonyl;
any one of which phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrrolidinyl, $C_2$–$C_6$ alkanoyl, or $C_1$–$C_4$ alkoxycarbonyl groups is unsubstituted or substituted with halo, $C_1$–$C_4$ alkyl, $C_1$–$C_4$ alkoxy, trifluoromethyl, amino, $C_1$–$C_4$ alkylamino, di($C_1$–$C_4$ alkyl)amino, or $C_2$–$C_4$ alkanoylamino;
or $R^1$ is amino, a leaving group, hydrogen, $C_1$–$C_4$ alkylamino, or di($C_1$–$C_4$ alkyl)amino;

$R^5$ is pyridyl, anilino-($C_1$–$C_6$ alkylidenyl)-, or anilinocarbonyl;
$R^8$ is hydrogen or $C_1$–$C_6$ alkyl; and
$R^3$ is phenyl, phenyl-($C_1$–$C_6$ alkylidenyl)-, $C_3$–$C_8$ cycloalkyl, $C_5$–$C_8$ cycloalkenyl, $C_1$–$C_8$ alkyl, naphthyl, $C_2$–$C_8$ alkenyl, or hydrogen;
any one of which $R^3$ groups except hydrogen is unsubstituted or substituted with one or two halo, $C_1$–$C_3$ alkoxy, $C_1$–$C_3$ alkylthio, nitro, trifluoromethyl, or $C_1$–$C_3$ alkyl groups;
provided that if $R^2$ is phenyl and $R^8$ is hydrogen, $R^1$ cannot be $C_1$–$C_4$ alkyl, phenyl, or hydrogen;
or a pharmaceutically acceptable salt or solvate thereof, in combination with one or more pharmaceutically acceptable carriers, excipients, or diluents therefor.

7. A method for the treatment or prevention of a physiological disorder associated with an excess of tachykinins, which method comprises administering to a mammal in need of said treatment an effective amount of a compound of the formula

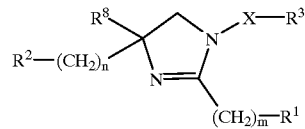

wherein:
m is 0 or 1;
n is 0 or 1;
X is —$(CHR^4)_p$—$(CHR^6)_q$—, where,
p is 0 or 1;
q is 0 or 1; and
$R^4$ and $R^6$ are independently selected from the group consisting of hydrogen and $C_1$–$C_3$ alkyl;
$R^2$ is phenyl, 2- or 3-indolyl, 2- or 3-indolinyl, benzothienyl, benzofuranyl, or naphthyl;
any one of which phenyl, 2- or 3-indolyl, 2- or 3-indolinyl, benzothienyl, benzofuranyl, or naphthyl groups is unsubstituted or substituted with one or two moieties independently selected from the group consisting of halo, $C_1$–$C_3$ alkoxy, trifluoromethyl, $C_1$–$C_4$ alkyl, phenyl-$C_1$–$C_3$ alkoxy, and $C_1$–$C_4$ alkanoyl groups;
$R^1$ is hydrogen, trityl, phenyl, diphenylmethyl, phenoxy, phenylthio, hexamethyleneiminyl, piperazinyl, piperidinyl, pyrrolidinyl, morpholinyl, indolinyl, indolyl, benzothienyl, benzofuranyl, quinolinyl, isoquinolinyl, tetrahydropyridinyl, reduced quinolinyl, reduced isoquinolinyl, phenyl-($C_1$–$C_6$ alkylidenyl)-, phenyl-($C_1$–$C_4$ alkoxy)-, quinolinyl-($C_1$–$C_6$ alkylidenyl)-, isoquinolinyl-($C_1$–$C_6$ alkylidenyl)-, reduced quinolinyl-($C_1$–$C_6$ alkylidenyl)-, reduced isoquinolinyl-($C_1$–$C_6$ alkylidenyl)-, benzoyl-($C_1$–$C_6$ alkylidenyl)-, $C_1$–$C_4$ alkyl, or —NH—$CH_2$—$R^5$;
any one of which $R^1$ groups is unsubstituted or substituted with halo, $C_1$–$C_4$ alkyl, $C_1$–$C_4$ alkoxy, trifluoromethyl, amino, $C_1$–$C_4$ alkylamino, or di($C_1$–$C_4$ alkyl)amino;
or any one of which $R^1$ groups is unsubstituted or substituted with phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrrolidinyl, $C_2$–$C_6$ alkanoyl, or $C_1$–$C_4$ alkoxycarbonyl;

any one of which phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrrolidinyl, $C_2$–$C_6$ alkanoyl, or $C_1$–$C_4$ alkoxycarbonyl groups is unsubstituted or substituted with halo, $C_1$–$C_4$ alkyl, $C_1$–$C_4$ alkoxy, trifluoromethyl, amino, $C_1$–$C_4$ alkylamino, di($C_1$–$C_4$ alkyl)amino, or $C_2$–$C_4$ alkanoylamino;

or $R^1$ is amino, a leaving group, hydrogen, $C_1$–$C_4$ alkylamino, or di($C_1$–$C_4$ alkyl)amino;

$R^5$ is pyridyl, anilino-($C_1$–$C_6$ alkylidenyl)-, or anilinocarbonyl;

$R^8$ is hydrogen or $C_1$–$C_6$ alkyl; and $R^3$ is phenyl, phenyl-($C_1$–$C_6$ alkylidenyl)-, $C_3$–$C_8$ cycloalkyl, $C_5$–$C_8$ cycloalkenyl, $C_1$–$C_8$ alkyl, naphthyl, $C_2$–$C_8$ alkenyl, or hydrogen;

any one of which $R^3$ groups except hydrogen is unsubstituted or substituted with one or two halo, $C_1$–$C_3$ alkoxy, $C_1$–$C_3$ alkylthio, nitro, trifluoromethyl, or $C_1$–$C_3$ alkyl groups;

or a pharmaceutically acceptable salt or solvate thereof.

8. A method as claimed in claim 7 employing a compound wherein $R^3$ is phenyl, or phenyl-($C_1$–$C_6$ alkyl)-, any one of which groups is unsubstituted or substituted with one or two chloro, fluoro, trifluoromethyl, methoxy, ethoxy, methyl, or ethyl groups.

9. A method as claimed in claim 8 employing a compound wherein $R^2$ is phenyl, 2-indolyl, 3-indolyl, 2-indolinyl, 3-indolinyl, or naphthyl, any one of which groups is unsubstituted or substituted with one or two chloro, fluoro, methyl, ethyl, methoxy, or ethoxy groups.

10. A method as claimed in claim 9 employing a compound wherein $R^1$ is hydrogen, phenyl, piperazinyl, piperidinyl, morpholinyl, benzofuranyl, phenyl-($C_1$–$C_4$ alkyl)-, phenyl-($C_1$–$C_4$ alkoxy)-, —NH—$CH_2$—$R^5$, any one of which groups is unsubstituted or substituted.

11. A method as claimed in claim 10 employing a compound wherein $R^1$ is hydrogen, 1-(4-phenyl)piperazinyl, 1-(4-cyclohexyl)piperazinyl, 1-(4-phenyl)piperidinyl, 1-(4-cyclohexyl)piperidinyl, 1-(4-isopropyl)piperazinyl, or 1-[4-(1-pipenidinyl)]piperidinyl.

12. A method as claimed in claim 11 wherein the physiological disorder associated with an excess of tachykinins is selected from the group consisting of anxiety, depression, psychosis, and schizophrenia.

13. A formulation as claimed in claim 6 employing a compound wherein $R^3$ is phenyl, or phenyl-($C_1$–$C_6$ alkyl)-, any one of which groups is unsubstituted or substituted with one or two chlioro, fluoro, trifluoromethyl, methoxy, ethoxy, methyl, or ethyl groups.

14. A formulation as claimed in claim 13 employing a compound wherein $R^2$ is phenyl, 2-indolyl, 3-indolyl, 2-indolinyl, 3-indolinyl, or naphthyl, any one of which groups is unsubstituted or substituted with one or two chloro, fluoro, methyl, ethyl, methoxy, or ethoxy groups.

15. A formulation as claimed in claim 14 employing a compound wherein $R^1$ is hydrogen, phenyl, piperazinyl, piperidinyl, morpholinyl, benzofuranyl, phenyl-($C_1$–$C_4$ alkyl)-, phenyl-($C_1$–$C_4$ alkoxy)-, —NH—$CH_2$—$R^5$, any one of which groups is unsubstituted or substituted.

16. A formulation as claimed in claim 15 employing a compound wherein $R^1$ is hydrogen, 1-(4-phenyl)piperazinyl, 1-(4-cyclohexyl)piperazinyl, 1-(4-phenyl)piperidinyl, 1-(4-cyclohexyl)piperidinyl, 1-(4-isopropyl)piperazinyl, or 1-[4-(1-piperidinyl)]piperidinyl.

\* \* \* \* \*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Phe Xaa Gly Leu Met
1               5

(2) INFORMATION FOR SEQ ID NO: 2:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 2:

Arg Pro Lys Pro Gln Gln Phe Phe Gly Leu Met
1           5                  10

(2) INFORMATION FOR SEQ ID NO: 3:

```
        (i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 3:

His Lys Thr Asp Ser Phe Val Gly Leu Met
1               5                   10

(2) INFORMATION FOR SEQ ID NO: 4:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 4:

Asp Met His Asp Phe Phe Val Gly Leu Met
1               5                   10
```